United States Patent [19]

Dunshee

[11] 4,233,976

[45] Nov. 18, 1980

[54] STYPTIC DEVICE

[75] Inventor: Wayne K. Dunshee, Maplewood, Minn.

[73] Assignee: Minnesota Mining and Manufacturing Company, St. Paul, Minn.

[21] Appl. No.: 922,488

[22] Filed: Jul. 6, 1978

Related U.S. Application Data

[63] Continuation of Ser. No. 747,083, Dec. 3, 1976, abandoned.

[51] Int. Cl.³ .............................................. A61M 7/00
[52] U.S. Cl. .................................... 128/260; 128/267; 128/156
[58] Field of Search ................................ 128/155–156, 128/163, 260, 267–269; 424/27–28, 154

[56] References Cited

U.S. PATENT DOCUMENTS

| | | |
|---|---|---|
| 2,512,616 | 6/1950 | Eberl et al. . |
| 2,517,772 | 8/1950 | Doub et al. . |
| 2,688,586 | 9/1954 | Eberl et al. . |
| 2,693,438 | 11/1954 | Ward . |
| 2,772,999 | 12/1956 | Masci et al. . |
| 2,923,298 | 2/1960 | Dockstader et al. . |
| 3,006,338 | 10/1961 | Davies . |
| 3,113,568 | 12/1963 | Robins . |
| 3,121,021 | 2/1964 | Copeland . |
| 3,122,479 | 2/1964 | Smith . |
| 3,206,361 | 9/1965 | Shelley et al. . |
| 3,285,245 | 11/1966 | Eldredge et al. ................... 128/156 |
| 3,287,222 | 11/1966 | Larde et al. ............. 424/28 |
| 3,297,032 | 1/1967 | Antonik ................. 128/268 |
| 3,328,259 | 6/1967 | Anderson ................... 424/28 |
| 3,342,183 | 9/1967 | Edenbaum ........... 128/216 |
| 3,366,112 | 1/1968 | Antonik ................. 128/268 |
| 3,428,043 | 2/1969 | Shepherd ............... 128/268 |
| 3,446,208 | 5/1969 | Fukuda ................. 128/156 |
| 3,528,417 | 9/1970 | Gardner et al. ..................... 128/156 |
| 3,579,628 | 5/1971 | Gander et al. .......................... 424/28 |
| 3,619,280 | 11/1971 | Schener ............. 15/210 A |
| 3,666,750 | 5/1972 | Briskin et al. ........... 536/56 |
| 3,678,933 | 7/1972 | Moore et al. ......... 128/296 |
| 3,703,897 | 11/1972 | Mack et al. ........... 128/156 |
| 3,709,221 | 1/1973 | Riely .................. 128/156 |
| 3,813,466 | 5/1974 | Anderson ................ 424/28 |
| 3,908,650 | 9/1975 | Dunshee et al. .................... 128/156 |
| 4,022,203 | 5/1977 | Ackley ................. 128/156 |

FOREIGN PATENT DOCUMENTS 936229 9/1963 United Kingdom .

Primary Examiner—C. Fred Rosenbaum
Attorney, Agent, or Firm—Cruzan Alexander; Donald M. Sell; Gary Griswold

[57] ABSTRACT

A styptic device capable of stopping bleeding in minor wounds without causing significant pain in the injured person comprising a porous web, at least about 50 microns thick, and comprising hydrophobic fibers, said web containing about 0.05 to 0.9 gram of styptic material per cubic centimeter of web.

7 Claims, No Drawings

STYPTIC DEVICE

This is a continuation of application Ser. No. 747,083 filed Dec. 3, 1976, and now abandoned.

This invention elates to a styptic device useful in stopping bleeding in minor wounds. Specifically, this invention relates to a styptic device which stops bleeding in such wounds but does not cause the user significant pain.

Styptic pencils have been used for years to stop bleeding of minor wounds; particularly cuts which occur on the face during shaving. Styptic pencils, while causing bleeding to stop in the wound because of the presence of alum, i.e., aluminum potassium sulfate or aluminum ammonium sulfate, cause significant pain to the user and often leave a large residue of alum on the surface of the skin.

Other means of stopping bleeding of wounds involve the use of tissue or cloth applied to the wound to cause stoppage of blood flow and clotting and application of a bandage to the wound. One approach is a styptic bandage described in U.S. Pat. No. 3,113,568 which describes including in a bandage styptic, clot-producing agents such as alum or salts of iron or the like. In that patent, the agent is to be located in the foam portion of the bandage or at the contact surface between the foam portion and the pad of the bandage. With the styptic bandage of that patent as well as with the aforementioned use of tissue or cloth, clot formation occurs within the tissue, cloth or bandage. When the bandage, cloth or tissue are removed, the clot is often also removed causing bleedng to commence once again. The styptic bandage of the U.S. Pat. No. 3,113,568 attempts to avoid this by having a portion of the foam tear off and remain with the clot upon removal of the bandage to allow the bandage to be removed without removing the clot.

Applicant has discovered a styptic device which stops the bleeding in minor wounds but does not cause a significant pain sensation in the injured person. When Applicant's device is removed from the wound site the clot is not removed for the clot or clots is or are substantially formed below the surface of the styptic device and not significantly attached to the device. Applicant's styptic device comprises (a) a porous web comprising hydrophobic fibers, said web being at least about 50 microns in thickness and (b) about 0.05 to 0.9 gram of styptic material per cubic centimeter of web contained within the web.

It is believed that the styptic device of the present invention operates by allowing blood to flow through the porous web of the device when the device is applied with a slight pressure to the wound site. This causes the styptic material contained within the web to be delivered by means of blood flow to the wound site which causes a vascular styptic effect, i.e., causes a contraction of the injured or divided blood vessels which are of a small caliber at the surface of the skin, and may also assist in clotting the blood by means of chemically assisted coagulation. The vascular styptic effect causes the blood to substantially slow down or cease and thus aid clot formation.

The porous web of the styptic device of the present invention can be either woven or nonwoven but is preferably nonwoven. The fibers which comprise the porous web are hydrophobic or water-repellent. The fibers can obtain their water repellency either from their inherent composition or through a sizing and/or bonding of them. In particular, the web can be a nonwoven web of synthetic fibers such as polyester, rayon and/or nylon. The web of these fibers is prepared using known procedures such as described in U.S. Pat. No. 3,121,021. The web is bonded with a suitable polymeric material such as latex of ethylene/acetate copolymer. This sizes or coats the fibers sufficiently so that the fibers have sufficient water repellency. The fibers of the web can be wood pulp which are sized, or mixtures of wood fibers and synthetic fibers such as those noted above. The web can also be woven fabric which would normally be sized so as to impart water repellency to the fibers.

The fibers of the web are required to be hydrophobic or water repellent, i.e., water repellent to the extent that water penetrates the fibers with difficulty in order that the styptic device does not stick to the wound and become encapsulated in the clot formed at the wound site. The water repellency of the fibers prevents the attachment of the device to the wound site. The porosity of the web allows for liquid, such as blood, to flow through the web as above described to form a liquid medium which allows the styptic material in the web to diffuse back to the wound site.

Particularly useful webs in the present invention include (1) a web which comprises the interlayer of the microporous medical adhesive tape described in U.S. Pat. 3,908,650 and (2) the backing of the surgical adhesive tape described in U.S. Pat. No. 3,121,021. If the web is a woven web of fibers and if the fibers inherently have sufficient water repellency, no sizing or bonding agent need be used. However, if a nonwoven web of fibers is used, the fibers are bonded together in order to give the interlayer structural integrity. If the fibers have sufficient water repellency inherently or are sized fibers, the web can be bonded by heat or spun-bonding or by using a bonding agent such as previously described. Fibers which are spun or heat-bonded can have a water repellency increased by the use of sizing material. The amount of material used will depend on the type of fiber and sizing agent. If the fibers of the web are not inherently sufficiently water repellent and are not previously sized, the sizing and bonding can be done by using a bonding agent such as previously described, i.e. ethylene/acetate copolymer latex ("Elvace" 1968, E. I. du Pont de Nemours and Company, Wilmington, Del.) or other binder/sizing materials such as water dispersible rubbery acrylate-polymer latices which dry on fibers to a nontacky state. These are well known. An example is "Rhoplex B-15" sold by Rohm & Haas Co., an aqueous dispersion containing about 46% acrylic polymer solids by weight and which is diluted with water to provide a sizing and bonding bath having a polymeric solids concentration of about 28%. The concentration is adjusted so that the weight of the polymeric sizing and bonding material on a dry basis is about 30 to 90%, preferably 50 to 80% of the total web weight prior to the addition of the styptic material. The above percentage applies when other binders or sizing agents are used. The amount used depends on the type of fibers and the type of binder.

A preferred web for use in the device of the present invention is a nonwoven web of compacted fibers formed of interlaced staple rayon (or equivalent) textile fibers (having a length of about 2.5 to 5 centimeters) which is unified by the impregnation with water-insoluble rubbery-fiber-binding/sizing agent (such as a rubbery acrylate polymer latex) that coats the individual fibers (without filling the interstices) and bonds them together at their crossing points; such as to result in a thin, pliable, inextensible, resilient water-resistant, translucent, porous, cloth-like fabric that is strong and tough enough for use as the web in the present invention and yet is finger tearable so that the styptic device can be applied from a roll without having to be cut. This unified nonwoven recticular fibrous web has a very large number of minute interfilar passageways per square centimeter and is highly porous. This porosity allows not only room for the styptic material when it is applied to the web and dried but also allows for the blood flow through the web.

The porous web normally is at least 50 microns in thickness. This provides a sufficient thickness of web to allow the styptic material to be incorporated therein. Normally the web would be less than 400 microns in thickness. Preferably, the web is 100 to 200 microns in thickness. Having a web that is too thick can result in an inability to cause blood flow through the web to an extent so that sufficient flow of the styptic material back to the wound site is impeded.

The styptic material utilized in the present invention is preferably of the vascular styptic type. That is, the type which causes contraction of the injured or divided blood vessels. The preferred styptic material is alum, i.e., aluminum potassium sulfate or aluminum ammonium sulfate. Sufficient styptic material is included within the porous web, i.e., on the surface of or in the porous web to provide a sufficient concentration of the styptic material to cause bleeding to stop at the wound site. Normally, an average of 0.05 to 0.9 gram of styptic material per cubic centimeter of web is contained within the web. This concentration of styptic material would normally cause, with most individuals, the stoppage of bleeding, in a minor wound without a significant pain sensation in the injured person. As the amount of styptic material becomes less, the pain sensation decreases but so does the ability to stop bleeding. As the concentration of styptic material increases, more significant pain sensation will be realized but enhanced hemostasis will occur. For most individuals the preferred range is from 0.25 to 0.40 gram of styptic material per cubic centimeter of web. This concentration allows for an insignificant pain sensation, but a sufficient stopping of bleeding.

Normally, the styptic material will be uniformly dispersed throughout the web. A very high concentration of styptic material at the surface of the web can cause a greater pain sensation. It is believed that the styptic material, in drying, tends to attach itself in microcrystalline form to the fibers of the web. It does not significantly fill the interstices of the web except at the higher concentration levels of styptic material. The attachment of the styptic material to the fibers of the web causes the web to become sterile because of the presence of the styptic material. This provides a styptic device which prevents bleeding without pain and also provides a device which is sterile in use.

The styptic material is placed in and on the web by means of passing the web through an aqueous solution of the styptic material either heated or at room temperature. Heated solutions allow higher concentrations of styptic material to be applied to the web. The saturated web is then dried either by use of heaters or at room temperature.

As discussed briefly above, the styptic device is utilized by tearing off a small piece of the web containing the styptic material and applying that to the cut or wound. The exudated blood from the cut penetrates the web and dissolves the styptic material which diffuses back through the blood to the wound surface. There is a slow and controlled diffusion of the styptic material. This not only reduces any pain sensation to the injured person, but also causes the styptic action at the wound surface producing contraction of the severed ends of the blood vessels, thereby reducing blood flow to a low level so that small, unobtrusive blood clots form directly at the blood vessel ends.

The following examples are meant to exemplify but not to limit the invention. All parts and percentages are by weight unless otherwise specified.

EXAMPLE I

A 12 pound per ream (20.4 grams/meter$^2$) nonwoven web of 1 ½ inch (3.81 centimeters), 1 ½ denier, type 400 Celanese polyester fibers (100% ethylene glycol terephthalate) (Celanese Fiber Co., Charlotte, N.C.) was prepared on a Garnett Carding Machine, Model 74C-120 (Proctor and Schwartz, Inc., Philadelphia, Pa.). During its preparation, the web was bonded with 12 pounds per ream (dry weight) (20.4 grams per meter$^2$) of copolymer binder as a 30% solids emulsion (Elvace, 1968, E.I., duPont de Nemours and Company, Wilmington, Del.) and then rebonded with 20 pounds per ream (dry weight) (33.9 grams/meter$^2$) Elvace 1968 as a 30% emulsion which also included 0.09% burnt umber and 0.5% raw sienna. (H. Kohnstamm & Co., Inc., 161 Avenue of the Americas, New York, N.Y.).

The aforesaid web which was approximately 100 microns thick was then dipped into a saturated 10% by weight aqueous solution of aluminum potassium sulfate (7 grams in 63 grams of water) at room temperature. Excess drops of the dipping solution were shaken off and the web was then dried in a 93° C. oven. The web contained 0.09 gram of aluminum potassium sulfate per cubic centimeter of web. 1"×3" (2.5 centimeters ×7.5 centimeters) strips of the aforesaid web containing the aluminum potassium sulfate were utilized to stop the bleeding in minor cuts without significant pain. Blood clots were formed but not removed when the web was removed from the wound site.

EXAMPLE II

A nonwoven web approximately 100 microns thick was prepared as set forth in the example of U.S. Pat. No. 3,121,021.

The aforesaid web was dipped into a hot 60° C. solution of aluminum potassium sulfate (2 grams in 7.2 milliliters of water). The web was hung and air dried. The web contained 0.21 gram of aluminum potassium sulfate per cubic centimeter of web. One centimeter ribbons approximately one meter long, were cut out and put on plastic cores and packaged in blister packs. Fellow employees were supplied with the packages. The impregnated web was applied to various superficial wounds by the employees with the result of generally effective stoppage of bleeding and insignificant or no pain.

EXAMPLE III

A web having a weight of 0.69 grams per 155 centimeters$^2$ and a thickness of approximately 100 microns was made as set forth in Example 2. The web was saturated with an aqueous 40% aluminum potassium sulfate solution. This was done using a continuous coating technique by passing the web under a glass bar which was submerged in the aluminum potassium sulfate solution. The solution was kept hot at 60° centigrade on a steam table. The web was passed through the solution and dried by means of three 750° F. (400° C.) hot air blowers at a rate of 91 centimeters per minute. The web was 9 inches (23 cm) wide. The resulting impregnated web contained an average of 28 ±2 grams of aluminum potassium sulfate per meter$^2$ or 0.28 gram of aluminum potassium sulfate per cubic centimeter of web.

After the aforesaid impregnated web had been exposed on the shelf of the lab for several weeks, two 4"×6"(10 cm × 15 cm) samples were cut from the web. Pieces (6.4 cm$^2$) of these samples were placed unsterilized on agar plates and incubated for 48 hours. There was no growth on the agar during this time.

The aforesaid samples were also subjected each to an agar plate which had been prepared and seeded with staphylococcus aureus microorganisms. After incubation for 24 hours, it was found that the zone of inhibition of growth existed for 1 millimeter around one of the disks and 3 millimeters around the other of the disks of the web. The sample with the smaller zone of inhibition has a 16.39 pound per ream weight (27.81 gm/m$^2$) of aluminum potassium sulfate whereas the other sample had a 17.21 pound per ream weight (29.20 gm/m$^2$).

What is claimed is:

1. A styptic device capable of causing bleeding to stop in a minor wound when said device is applied to the wound without causing a significant pain sensation in the injured person and without significantly attaching to any clot formed in stopping said bleeding comprising:
   (a) a porous web comprising hydrophobic fibers, said web being at least about 50 microns in thickness, and
   (b) about 0.05 to 0.90 gram of styptic material per cubic centimeter of web contained within said web, said styptic material being releasably attached in crystalline form to said hydrophobic fibers whereby said bleeding forms a liquid medium allowing said styptic material to diffuse back to the wound site to cause a vascular styptic effect.

2. The styptic device of claim 1 wherein said styptic material is aluminum potassium sulfate.

3. The styptic device of claim 1 wherein said styptic material is aluminum ammonium sulfate.

4. The styptic device of claim 1 wherein said web contains 0.25 to 0.40 gram of said styptic material per cubic centimeter of web.

5. The styptic device of claim 1 wherein said web is a nonwoven web comprising sized synthetic fibers.

6. The styptic device of claim 4 wherein said web is a nonwoven web comprising sized synthetic fibers.

7. The styptic device of claim 6 wherein said styptic material is aluminum potassium sulfate.

* * * * *